United States Patent [19]

Hill et al.

[11] Patent Number: 5,403,356

[45] Date of Patent: Apr. 4, 1995

[54] METHOD AND APPARATUS FOR PREVENTION OF ATRIAL TACHY ARRHYTHMIAS

[75] Inventors: Michael Hill, Brooklyn Park; Rahul Mehra, Stillwater, both of Minn.

[73] Assignee: Medtronic, Inc., Minneapolis, Minn.

[21] Appl. No.: 53,772

[22] Filed: Apr. 28, 1993

[51] Int. Cl.$^6$ ............................................. A61N 1/362
[52] U.S. Cl. ........................................... 607/14; 607/4
[58] Field of Search ...................... 607/4, 5, 17, 14, 15, 607/28

[56] References Cited

U.S. PATENT DOCUMENTS

| | | |
|---|---|---|
| 3,937,226 | 2/1976 | Funke . |
| 4,088,140 | 5/1978 | Rockland . |
| 4,354,497 | 10/1982 | Kahn . |
| 4,817,605 | 4/1989 | Sholder ................................. 607/28 |
| 5,027,815 | 7/1991 | Funke et al. . |
| 5,273,035 | 12/1993 | Markowitz et al. ................... 607/14 |
| 5,282,837 | 2/1994 | Adams et al. ............................ 607/5 |

OTHER PUBLICATIONS

"Does Dual Chamber or Atrial Pacing Prevent Atrial Fibrillation? The Need for a Randomized Controlled Trial", by Lamas et al., in PACE, vol. 15(8), Aug., 1992.

"Validation of Double-Spike Electrograms as Markers of Conduction Delay or Block in Atrial Flutter", by Cosio et al., in the American Journal of Cardiology, Apr. 1, 1988, vol. 61.

"Demonstration of Macroeentry and Feasibility of Operative Therapy in the Common Type of Atrial Flutter", by Klein et al., in Mar. 1, 1986, The American Journal of Cardiology, vol. 57.

*AHA 1991, Abstracts from the 64th Scientific Sessions* #1804 "Simultaneous Dual Atrium Pacing in High Degree Intrarterial Blocks: Hemodynamic Results" Dauber et al.

*PACE* vol. 14, Apr. 1991, Part II, p. 648, "Prevention of Atrial Tachyarrhythmias Related to Advanced Interarterial Block by Permanent Atrial Resynchronization" Mabo et al. #122.

*PACE*, vol. 14, Apr. 1991, Part II, p. 650, "Hemodynamic Benefits of Permanent Atrial Resynchronization in Patients with Advanced Interatial Blocks, Paced in DDD Mode", Daubert, et al. #130.

*PACE* vol. 15, Apr. 1992, Part II, "Renewal of Permanent Left Atrial Pacing Via the Coronary Sinus", p. 572, #255.

*PACE*, vol. 16, Apr. 1993, Part II, p. 885, "Permanent Dual Atrium Pacing in Major Interatrial Conduction Blocks: A Four Years Experience", Daubert, et al., #141.

*Primary Examiner*—William E. Kamm
*Assistant Examiner*—Scott M. Getzow
*Attorney, Agent, or Firm*—Reed A. Duthler; Harold R. Patton

[57] ABSTRACT

A method and apparatus for pacing the atrium to reduce the incidence of dangerous arrhythmias. Electrodes are located at least two locations within the atrium, preferably in the triangle of Koch and/or an area of prolonged effective refractory period elsewhere within the atrium. Additional or alternative electrode locations may also be employed. The apparatus defines a variable interval following atrial depolarizations, based on the detected rate of the depolarizations. In response to a sensed depolarization at one of the locations, outside the variable interval, pacing pulses are delivered at least to the electrodes located at the other locations. Demand atrial pacing using some or all electrodes is also provided.

26 Claims, 5 Drawing Sheets

METHOD AND APPARATUS FOR PREVENTION OF ATRIAL TACHY ARRHYTHMIAS

BACKGROUND OF THE INVENTION

The present invention relates generally to the field of implantable stimulators and more particularly to cardiac pacemakers and implantable antiarrhythia devices.

Atrial fibrillation or flutter is a common arrhythmia that is typically controlled by means of drug therapy. Over the years, there have been proposals for atrial cardioverters and defibrillators, which, in a fashion similar to the implantable cardioveter/defibrillators presently available for use in the ventricle, would terminate atrial fibrillation or flutter by means of a high voltage electrical shock.

Some retrospective studies have indicated that the presence of a pacemaker in the atrium (for example an AAI, VDD or DDD pacemaker) may reduce the incidence of atrial fibrillation, by maintaining a regular atrial rate. For example, see Lamas, G. A., et al. PACE, Vol. 15, August, 1992, pp. 1109-1113. In such applications, pacing leads are typically placed in the right atrial appendage.

It has also been proposed to reduce the incidence of ventricular fibrillation in the ventricle by using multiple site pacing. For example, in U.S. Pat. No. 3,937,226, issued to Funke, multiple electrodes are provided for location around the ventricles. In response to a sensed depolarization following a refractory period, at any of the electrodes, all electrodes are paced. All electrodes are similarly paced in the absence of sensed depolarizations for a period of 1000 ms. U.S. Pat. No. 4,088,140 issued to Rockland et al discloses a similar device, in which a pacing pulse is delivered only to a single electrode in response to a failure to sense during a 1000 ms period, and delivery of pacing pulses to multiple electrodes is triggered in response to sensed depolarizations occurring between 150 and 500 ms following delivery of a previous sensed depolarization or pacing pulse. U.S. Pat. No. 4,354,497, issued to Kahn adds sensing electrodes adjacent the septum of the heart and delivers pacing pulses to multiple electrodes spaced around the ventricles in response to sensed depolarizations at the ventricular electrodes which are not preceded by depolarizations sensed at the septum electrodes.

Cardiac potential mapping studies have shown that a portion of the atrium known as the "triangle of Koch" frequently exhibits double spiked and fractionated electrograms and may be subject to reduced conduction speed. For example, see Cossio, F. G. et al., *American Journal of Cardiology*, 1988, 61: 775-780, Kline, G. J. et al., *American Journal of Cardiology*, 1968; 57: 587-591. The triangle of Koch is a portion of the right atrium, containing the AV node, limited distally by the septal attachment of the tricuspid valve and proximally by the sinus septum. Cardiac mapping studies may also be employed to identify other areas of the atrium which display refractory periods longer than in the remainder of the atrium, in individual patients.

Summary of the Invention

The present invention is directed toward preventing the occurrence of atrial fibrillation. The disclosed embodiment of the invention pursues this desired result by means of electrodes located at desired site or sites within the atrium. Preferably, electrodes are located in the triangle of Koch, in an area of prolonged refractory period, or both. Electrodes may also be located in other areas of the atrium suitable for pacing and sensing. While the disclosed embodiments employ two pairs of electrodes, use of more than two pairs of electrodes is also believed to be within the scope of the invention. Use of a single electrode pair, located at a desired site such as the triangle of Koch and used for both sensing and pacing is also believed to be within the scope of the invention.

One method of practicing the invention employs a first electrode pair located in either the triangle of Koch or an area of prolonged refractory period and a second electrode pair located elsewhere in the atrium at a location appropriate for pacing and sensing, such as the right atrial appendage. A second method of practicing the invention employs electrodes located in both the triangle of Koch and an area of prolonged refractory period.

In the disclosed embodiments, both pairs of electrodes are employed for demand pacing in the atrium. In the event that the atrial rhythm drops below a preset rate defined by the pacemaker, pacing pulses are delivered to both electrodes pairs. In addition, in response to sensing of an atrial depolarizations by one of the electrode pairs, pacing pulses are delivered either to the other electrode pair or to both electrode pairs. The pacing pulses may be delivered essentially simultaneously with the detection of the atrial depolarizations, or may be delivered following a short delay period, e.g. less than 50 ms.

In the preferred embodiments of the invention, in order to reduce the possibility that the delivered pacing pulses might induce an arrhythmia, following an atrial pacing pulse or a sensed atrial depolarization, a minimum time interval (APB interval) is defined. If an atrial depolarization occurs within the APB interval, it is classed as an atrial premature beat, the escape interval of the pacemaker is reset, but no pacing pulses are triggered.

In the preferred embodiments of the invention, the APB interval is defined as a function of the preceding atrial rate, with the APB interval being based on the duration of a preceding interval or intervals between atrial depolarizations. For example, the APB interval may be based on the average interval separating preceding atrial sensed or paced depolarizations, (average A—A interval). More particularly, the APB interval may be equal to the average A—A interval minus a predetermined interval or may be proportional to the average A—A interval, e.g. 50%. Sensed events occurring in APB intervals are not employed to calculate the average A—A interval.

DETAILED DESCRIPTION OF THE PREFERRED EMBODIMENTS

Figure 1:
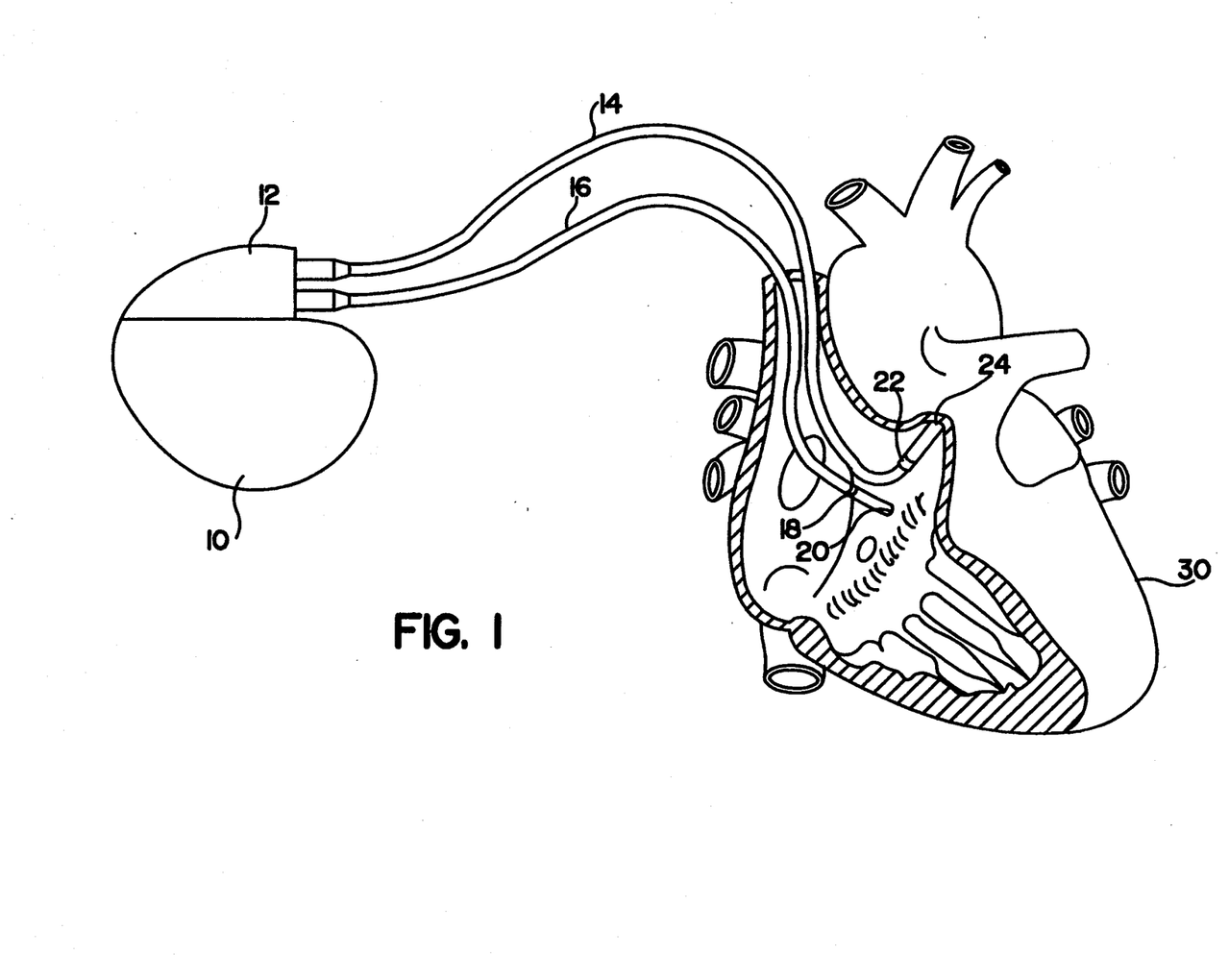
FIG. 1 is a drawing illustrating the interconnection of a cardiac pacemaker according to the present invention with the right atrium of a human heart.

FIG. 1 shows an implantable pacemaker 10, according to the present invention, and its interconnection to a human heart 30. The pacemaker is provided with two leads 14 and 16, coupled to the pacemaker by means of a connector block 12. Leads 14 and 16 take the form of bipolar endocardial screw-in leads, of the type presently available and widely marketed for use in conjunction with cardiac pacemakers. These leads are each provided with ring electrodes (18, 22) and are each provided with an extendable helical coil electrode, adjacent their distal ends (20, 24). The coil electrodes are not visible in this view, as they are screwed into the heart tissue.

The helical electrode adjacent the distal end 20 of lead 16 is screwed into the tissue of the right atrium, in the triangle of Koch area as defined above. Pacing and sensing using this lead is accomplished using ring electrode 18 and the helical electrode adjacent the distal end 20 of the lead. Lead 14 is attached to the right atrial appendage. Lead 14 is similarly employed to sense and pace the atrium using electrode 22 and the helical electrode adjacent the distal end 24. As discussed above, other electrode locations within the atrium may also be employed in conjunction with the present invention. For example, electrodes located in the triangle of Koch may be employed in conjunction with electrodes located in an area displaying prolonged refractory periods or electrodes located in an area displaying prolonged refractory periods may be employed in conjunction with electrodes located elsewhere in the right atrium. Alternatively, three or more electrode locations may be employed.

Figure 2:
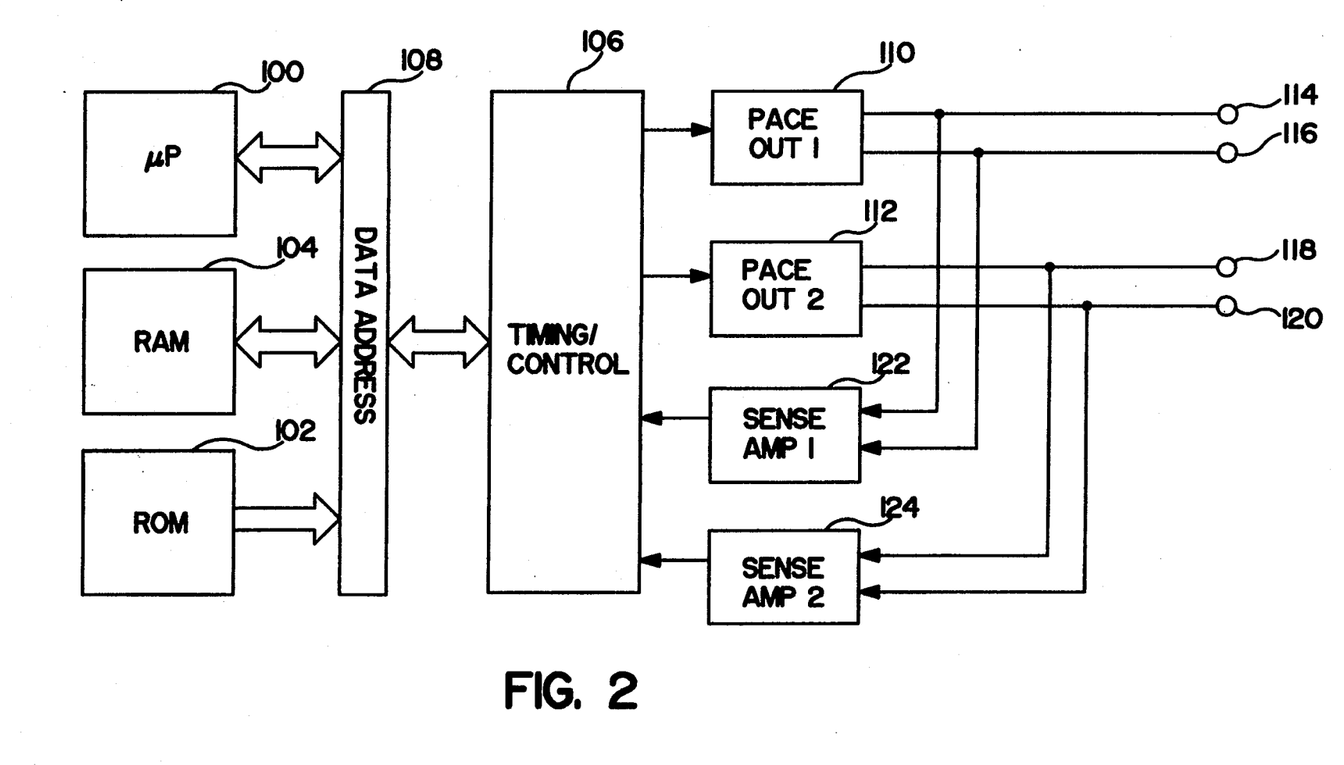
FIG. 2 is a block functional diagram of a cardiac pacemaker appropriate for use in practicing the present invention.

FIG. 2 is a block, functional diagram of a pacemaker appropriate for use in conjunction with the present invention. Because the diagram as illustrated makes use of presently available components and circuitry, only the basic functional operation as it relates to the present invention is described in detail. As a practical matter, it is believed that any of the available microprocessor controlled dual chamber (DDD, VDD) pacemakers presently on the market can readily be modified to practice the present invention, as they typically include all of the basic functional components illustrated.

In the embodiment illustrated, operation of the pacemaker is controlled by the microprocessor 100, under control of programming stored in read only memory (ROM) 102. Random access memory (RAM) 104 serves to store those parameters which are programmable by the physician, to store measurements made by the pacemaker and values calculated by the microprocessor. The RAM 104 may also be employed to store electrograms sensed by the pacemaker.

Microprocessor 100 is coupled to timing and control circuitry 106 by means of a data/address bus 108. Timing and control circuitry 106 takes the form of a number of counters or timers for defining the time intervals discussed below in conjunction with FIG. 3. The time intervals provided are intended to be programmable and to be varied under control of microprocessor 100.

Pulse generator 110 is coupled to electrodes 114 and 116, which may correspond to the electrodes located on lead 14, in FIG. 1. In particular, electrode 114 may correspond to ring electrode 22, and electrode 116 may correspond to the helical electrode adjacent distal end 24 of lead 14. Pulse generator circuitry 112 is coupled to electrodes 118 and 120, which correspond to the electrodes on lead 16 (FIG. 1 ). In particular, electrode 118 may correspond to ring electrode 118, and electrode 120 may correspond to the helical electrode adjacent the distal 20 of lead 16, in FIG. 1. Sense amp 122 is coupled to electrodes 114 and 116. Sense amp 124 is coupled to electrodes 118 and 120.

Timing/control circuitry 106, in the context of the present invention, defines a number of basic timing intervals. The first timing interval is the escape interval, corresponding to basic pacing rate of the device, as is conventional in cardiac pacemakers. In response to time-out of the escape interval, timing/control circuitry 106 triggers pulse generators 110 and 112 to deliver cardiac pacing pulses. Time out of the escape interval also serves as an interrupt, triggering microprocessor 100 to perform any necessary calculations or updating and to reset the timers within timing/control circuitry 106.

Also defined by timing/control circuit 106 are blanking and refractory periods, corresponding functionally to blanking and refractory periods in traditional cardiac pacemakers and applicable to both sense amps 122 and 124. During the blanking period, sense amps 122 and 124 are disabled. During the portion of the refractory period extending beyond the blanking period, sense amps 122 and 124 are enabled. However, atrial depolarizations sensed by either sense amp during this period will not function to reset the basic rate interval. During the refractory period, sensing for noise or other interference may also be conducted, as currently done in conjunction with presently available cardiac pacemakers. In the event that a delay is provided between the sensing of depolarizations and delivery of pacing pulses, the control/timing circuitry would function to time this delay as well.

Timing/control circuitry 106 also defines the variable atrial premature beat (APB) interval. The APB interval is a function of the measured atrial rate, over a preceding series of beats. For example, APB may be approximately one-half of the average interval separating atrial depolarizations, over a preceding series of 8 beats. In response to an atrial depolarization sensed by amplifier 122, following the APB interval, timing/control circuitry 106 may trigger only pulse generator 112 to deliver a pacing pulse or may trigger both pulse generators 110 and 112 to deliver pacing pulses. Similarly, in response to an atrial depolarization sensed by amplifier 124, outside the APB interval, timing/control circuitry 106 may trigger only pulse generator 110 to deliver a pacing pulse or may trigger both pulse generators 110 and 112 to deliver pacing pulses. In addition, in response to a sensed atrial alepolarization following the APB interval, timing/control circuitry 106 interrupts microprocessor 100, which in turn updates a running average of the preceding series of intervals between sensed and paced atrial depolarizations, based on the time of occurrence of the most recent depolarization. Microprocessor 100 then recalculates a new APB, based on the updated average. In response to a depolarization sensed by amplifier 122, within the APB period, microprocessor 100 is interrupted, and the escape interval, blanking interval, refractory interval and APB intervals timed by control/timing circuitry 106 are reset. However, the A—A interval ending in the premature atrial beat is not employed to update the running average of the atrial rate, and timing/control circuitry 106 does not trigger pulse generator 112 to deliver a pacing pulse or pulses.

In the event that the escape interval times out, triggering delivery of pacing pulses by output circuits 110 and 112, microprocessor 100 is interrupted, and the escape interval is used to update the average A—A interval, purposes of calculating a new value of the APB interval.

Figure 3:
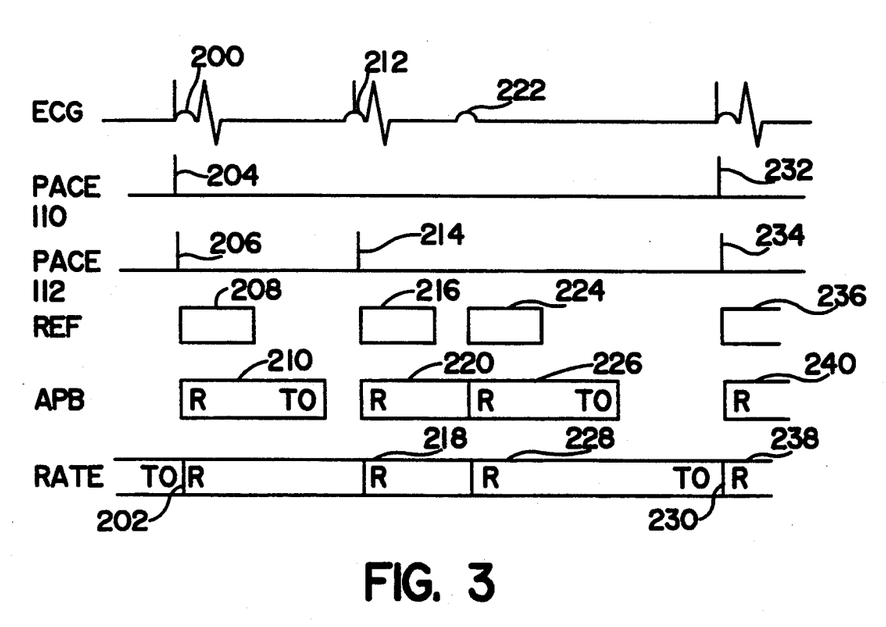
FIG. 3 is a simulated electrogram tracing in conjunction with a timing chart, indicating the operation of the various time intervals defined by a pacemaker according to a first embodiment of the invention.

FIG. 3 illustrates a simulated electrocardiogram (ECG) and associated timing charts, showing the interrelation of the various time intervals defined by the apparatus of FIG. 2. The simulated ECG begins with a paced atrial depolarization at 200. This event occurs as the result of a time out of the base pacing rate interval at 202, triggering pacing pulses delivered by both pulse generators (PACE 110 and PACE 112) at 204 and 206, respectively. Also illustrated are the refractory interval 208, initiated in responses to delivery of pacing pulses at 204 and 206 and the APB interval 210, similarly initiated following delivery of pacing pulses. APB interval 210 is updated by the microprocessor, following delivery of the pacing pulses, and extends for a predetermined period corresponding to a proportion or fraction of the current average atrial rate (excluding premature atrial beats).

At 212, a spontaneous atrial depolarization is sensed by sense amp 122. Because depolarization 212 follows the expiration of APB interval 210, a pacing pulse 214 is delivered by pulse generator 112. Alternatively, pacing pulses may be delivered by both pulse generators, as discussed above. The refractory interval 216 and escape interval 218 are restarted, and the APB interval 220 is updated by the microprocessor and correspondingly restarted. At 222, a premature atrial beat occurs, coming before time-out of APB interval 220. In response to the atrial premature beat 222, the refractory period 224, APB period 226 and escape interval 228 are all restarted. However, APB interval 226 is not updated to take into account the interval between depolarizations 212 and 222.

At 230, the basic rate interval times out, triggering delivery of pacing pulses 232 and 234, by both pulse generators. The refractory interval 236 and the escape interval 238 are both restarted. The APB interval 240 is updated to reflect the A—A interval (the escape interval) between spontaneous depolarization 222 and delivery of the cardiac pacing pulses at 232, 234.

Figure 4:
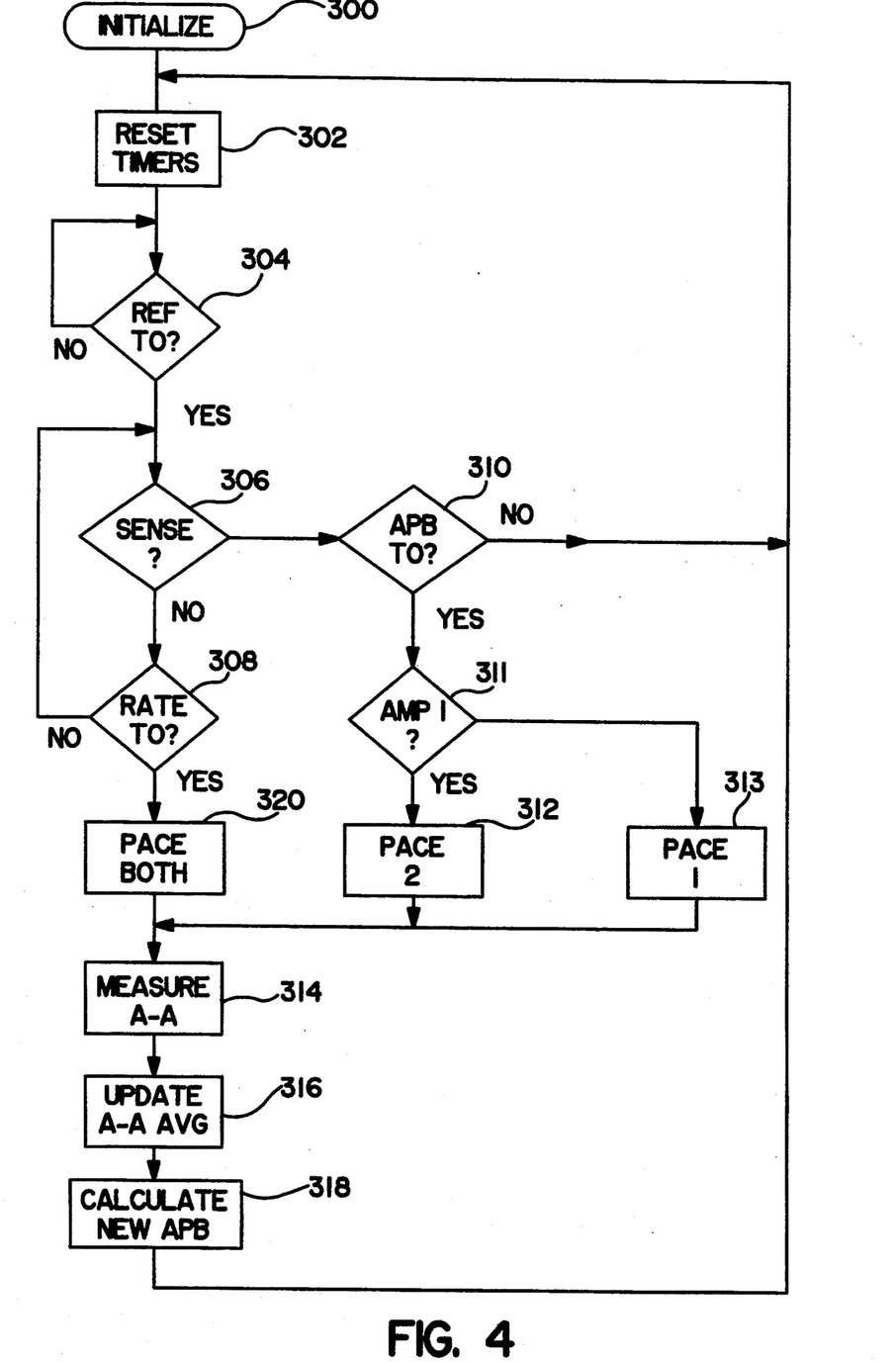
FIG. 4 is a functional flowchart, illustrating the basic operation of a pacemaker according to according to a first embodiment of the invention.

FIG. 4 is a functional flow chart illustrating the operation of the device of FIG. 2, as it practices the present invention. At 300, the device is initialized. This may correspond to initial hookup of the device to the battery, or to reprogramming of the device by physician.

At 302 the microprocessor is awakened, resetting the time intervals in the control/timing circuitry, including the blanking interval, refractory interval, APB interval and escape interval. At 304 the device waits until the refractory interval is timed out. When the refractory interval is timed out, the device awaits the occurrence of an atrial sense event at 306 or time out of the escape interval at 308. If an atrial depolarization is sensed by either sense amp, the device checks at 310 to determine whether the APB interval has timed out. This may be accomplished by the microprocessor, or by fixed logic within the timing/control circuitry. If the APB interval has not timed out at the time the atrial depolarization is sensed, the device is simply reset at 302, and the average A—A interval and APB intervals remain unchanged. If the APB interval has timed out when the atrial depolarization is sensed, the device checks at 311 to determine which sense amp detected the depolarization. In response, a pacing pulse is delivered to electrodes coupled to the other of the sense amps at 312 or 313. The pacing pulse may be delivered essentially simultaneously with the detection of the atrial depolarization, or may be delivered following a short delay period, e.g. less than 50 ms.

The microprocessor then measures the time interval since the last paced or sensed depolarization at 314. This may conveniently be accomplished by reading the count in the escape interval counter within the control/timing circuitry. The measured A—A interval is used at 316 to update the A—A average, and a new APB interval is calculated at 318, after which the device is reset at 302 to begin timing the next set of intervals.

In the event that no atrial depolarizations are sensed prior to timeout of the basic rate interval, as indicated at 308, both pulse generators are activated at 320. The microprocessor updates the A—A average using the escape interval as the measured A—A interval, calculates a new APB interval at 318, and the device is reset at 302.

Figure 5:
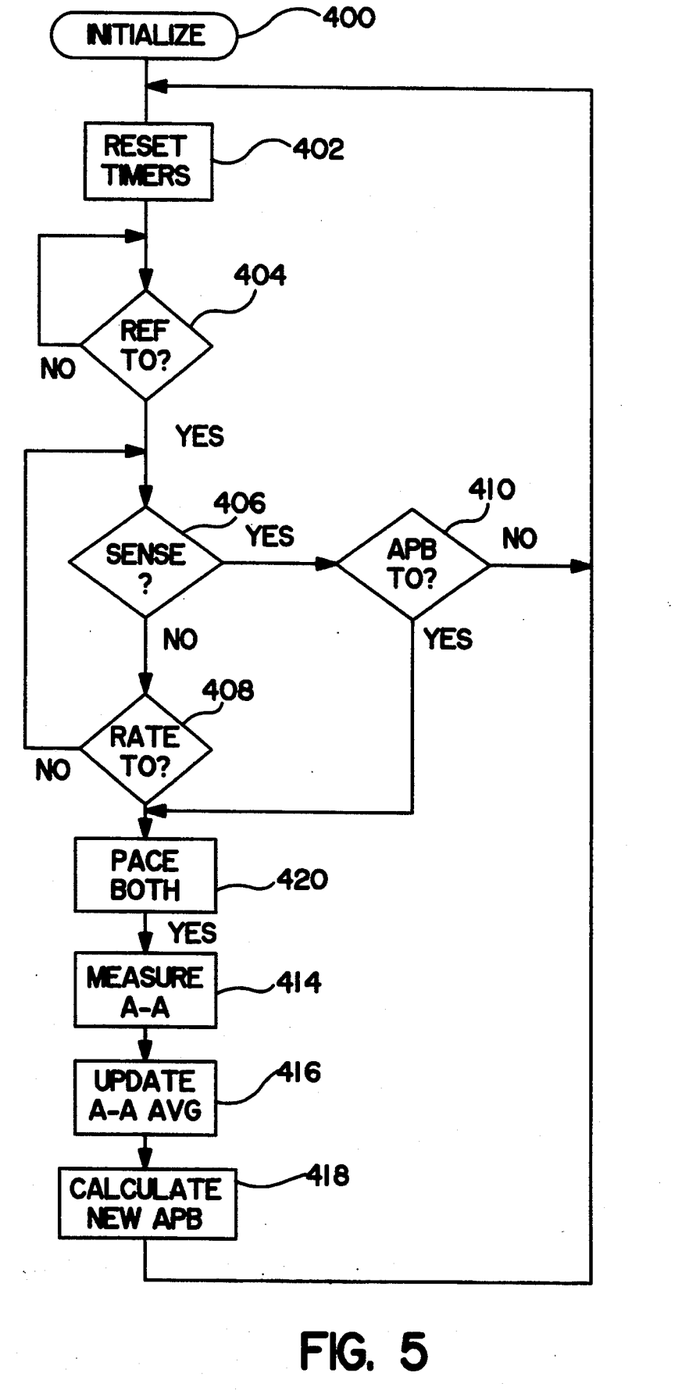
FIG. 5 is a functional flowchart, illustrating the basic operation of a pacemaker according to according to a second embodiment of the invention.

FIG. 5 illustrates the functional operation of a second embodiment of the device. The functional steps employed are a subset of those employed in FIG. 4, with functional blocks labelled in corresponding fashion. Blocks 400, 402 and 404 correspond to blocks 300, 302 and 304 in FIG. 4, and so forth. The difference in overall operation between devices according to FIG. 5 as opposed to devices which function as described in conjunction with FIG. 4 is that both pulse generators are activated every time pacing pulses are delivered in response to sensing of an atrial depolarization, regardless of which sense amplifier sensed the depolarization. Otherwise, a device according to FIG. 5 corresponds precisely to a device which functions as described in conjunction with FIG. 4.

The basic operation of pacemakers according to FIGS. 4 and 5 can readily be extended to apply to systems employing three or more electrode locations. In response to a sensed depolarization at any of the electrodes, pacing pulses may be applied to all electrodes or only to the electrodes other than those through which the depolarization was sensed.

While the embodiment disclosed above employs separate sense amps and pulse generators for each electrode pair, It is believed within the scope of the present invention to employ fewer sense amps and pulse generators, so long as the required functions are present. For example, a single pulse generator could supply all electrodes with pacing pulse, with switching circuits to direct pulses to the desired electrodes or electrode pairs. Similarly, by switching, time multiplexing or other means, one sense amp could be shared by two or more electrodes or electrode pairs.

Further, while it is believed that for practical purposes, commercial implementations of devices employing the present invention will generally take the form of microprocessor controlled pacemakers, the invention and its associated functions may also readily be practiced by means of a pacemaker based on full custom digital integrated circuitry as widely practiced in the pacing industry, or may even be practiced in the form of a device fabricated of commercially available discrete components and circuits, so long as basic functions set forth above are preserved. Therefore, the disclosed embodiments should be considered exemplary, rather than limiting with regard to the claims that follow.

In conjunction with above disclosure, we claim:

1. A method of pacing the atrium, comprising:
   sensing depolarizations of the atrium; and
   in response to sensing depolarizations of the atrium, applying cardiac pacing pulses to the triangle of Koch.

2. A method of pacing the atrium, comprising:
   selecting a location within a patient's atrium at which atrial tissue has an effective refractory period prolonged relative to tissue at other locations within said atrium;
   locating a pacing electrode at said location;
   sensing atrial depolarizations; and
   in response to sensing atrial depolarizations, applying cardiac pacing pulses to said pacing electrode.

3. A method according to claim 1 or claim 2 wherein said step of sensing depolarizations comprises sensing depolarizations between a first pair of electrodes and wherein said step of applying said pacing pulses comprises applying said pacing pulses between a second pair of electrodes.

4. A method according to claim 3 wherein said step of applying pacing pulses comprises applying pacing pulses to said first and second electrode pairs.

5. A method according to claim 1 or claim 2 wherein said step of sensing atrial depolarizations comprises sensing depolarizations between a pair of electrodes and wherein said step of applying said pacing pulses comprises applying said pacing pulses between said pair of electrodes.

6. A method according to claim 1 or claim 2 further comprising the steps of:
   determining atrial depolarization rate; and
   defining variable intervals following atrial depolarizations as a function of the determined atrial depolarization rate; and
   wherein said step of applying pacing pulses comprises applying pacing pulses only in response to sensed atrial alepolarizations occurring outside of said variable intervals.

7. A method according to claim 6 further comprising the steps of; defining escape intervals initiated in response to sensed atrial depolarizations; and applying pacing pulses in response to expiration of said escape intervals.

8. A method according to claim 1 or claim 2 wherein said step of applying cardiac pacing pulses comprises applying pacing pulses to multiple locations within the right atrium.

9. A method according to claim 1 or claim 2 wherein said step of applying cardiac pacing pulses comprises applying said pulses following a delay after sensing depolarizations of said atrium.

10. A method of pacing the atrium, comprising:
    locating electrodes at first and second locations within said atrium;
    sensing depolarizations of the atrium at said first and second locations;
    measuring intervals separating sensed depolarizations of said atrium;
    defining variable intervals following said sensed atrial depolarizations as a function of said measured intervals;
    in response to a sensed depolarization of said atrium at one of said first and second locations, outside of a said variable interval, applying a cardiac pacing pulse to the other of said first and second locations.

11. A method of pacing the atrium, comprising:
    locating electrodes at first and second locations within said atrium;
    sensing depolarizations of the atrium at said first and second locations;
    measuring the intervals separating sensed depolarizations of said atrium;
    defining variable intervals following said sensed atrial depolarizations as a function of said measured intervals;
    in response to a sensed depolarization of said atrium at one of said first and second locations, outside of a said variable interval, applying a cardiac pacing pulse to both said first and second locations.

12. A method according to claim 10 or claim 11 wherein said step of applying a cardiac pacing pulse comprises applying said pulse following a delay after a sensed depolarization of said atrium.

13. A method of pacing the atrium, comprising:
    locating electrodes at first and second locations within said atrium;
    sensing depolarizations of said atrium at said first and second locations;
    measuring intervals separating sensed depolarizations of said atrium;
    defining first intervals following sensed depolarizations of said atrium;
    delivering pacing pulses to said atrium, on expiration of said first intervals;
    defining second intervals shorter than first intervals, following sensed atrial alepolarizations;
    in response to a sensed depolarization of the atrium at one of said first and second locations, outside of a said second interval, applying a cardiac pacing pulse to the other of said first and second locations and restarting a said first interval; and
    in response to a sensed atrial depolarization within a said second interval, restarting a said first interval without applying a cardiac pacing pulse.

14. A method of pacing the atrium, comprising:
    locating electrodes at first and second locations within said atrium;
    sensing depolarizations of said atrium at said first and second locations;
    measuring intervals separating sensed depolarizations of said atrium;
    defining first intervals following sensed depolarizations of said atrium;
    delivering pacing pulses to said atrium, on expiration of said first intervals;
    defining second intervals shorter than first intervals, following sensed atrial depolarizations;
    in response to a sensed depolarization of the atrium at one of said first and second locations, outside of a said second interval, applying a cardiac pacing pulse to both said first and second locations.

15. A method of pacing the atrium, comprising:
    locating electrodes at first and second locations within said atrium;
    sensing depolarizations of said atrium at said first and second locations;
    measuring intervals separating sensed alepolarizations of said atrium;

defining first intervals following sensed depolarizations of said atrium;
delivering cardiac pacing pulses on expiration of said first intervals to both said first and second locations
defining second intervals shorter than first intervals, following sensed atrial depolarizations;
in response to a sensed depolarization of the atrium at one of said first and second locations, outside of a said second interval, applying a cardiac pacing pulse to the other of said first and second locations and restarting a said first interval; and
in response to a sensed atrial depolarization within a said second interval, restarting a said first interval without applying a cardiac pacing pulse.

16. A method according to claim 13 or claim 14 or claim 15 wherein said step of applying a cardiac pacing pulse comprises applying said pulse following a delay after a sensed depolarization of said atrium.

17. Apparatus for pacing the atrium, comprising:
first and second electrode means for location at first and second locations within the atrium;
means coupled to said first and second electrode means for sensing depolarizations of said atrium at said first and second locations;
means for measuring intervals separating sensed alepolarizations of said atrium;
means for defining variable time intervals following said sensed atrial depolarizations as a function of said measured intervals;
means coupled to said sensing means, responsive to an atrial depolarization sensed at either of said first and second locations outside of a said variable interval, for applying a cardiac pacing pulse to one of said first and second electrode means located at the other of said first and second locations.

18. An apparatus for pacing the atrium, comprising:
first and second electrode means for location at first and second locations within the atrium;
means coupled to said first and second electrode means for sensing depolarizations of said atrium at said first and second locations;
means for measuring intervals separating sensed depolarizations of said atrium;
means for defining variable time intervals following said sensed atrial depolarizations as a function of said measured intervals;
means coupled to said sensing means, responsive to an atrial depolarization sensed at one of said first and second locations outside of a said variable interval, for applying a cardiac pacing pulse to both of said first and second electrode means.

19. Apparatus according to claim 17 or claim 18 further comprising means for defining escape intervals following sensed atrial depolarizations and wherein said responsive means further comprises means responsive to expiration of a said escape interval, for applying a cardiac pacing pulse to one of said first and second electrode means.

20. An apparatus according to claim 19 wherein said responsive means comprises means for applying a cardiac pacing pulse to both of said first and second electrode means in response to expiration of a said escape interval.

21. An apparatus according to claim 17 or claim 18 wherein said responsive means comprises means for applying a cardiac pacing pulse following a delay after a sensed depolarization of said atrium.

22. An apparatus for pacing the atrium, comprising:
first electrode means for location at a first location in the atrium;
second electrode means for location at a second location in the atrium;
means coupled to said first and second electrode means for sensing depolarizations of said atrium at said first and second locations;
means for measuring intervals separating sensed depolarizations of said atrium;
first timing means for defining first intervals initiated in response to sensed depolarizations of said atrium;
pulse generator means for applying a cardiac pacing pulse to both of said first and second electrode means in response to expiration of a said first time interval
second timing means for defining second intervals shorter than said first intervals, following sensed atrial depolarizations;
means responsive to a sensed depolarization of the atrium at one of said first and second locations, outside of a said second interval, for triggering said pulse generator to apply a cardiac pacing pulse to the one of said first and second electrodes located at the other of said first and second locations and for restarting a said first interval and responsive to a sensed atrial depolarization within a said second interval for restarting a said first interval without triggering said pulse generator means to apply a cardiac pacing pulse.

23. An apparatus for pacing the atrium, comprising:
first electrode means for location at a first location in the atrium;
second electrode means for location at a second location in the atrium;
means coupled to said first and second electrode means for sensing depolarizations of said atrium at said first and second locations;
means for measuring intervals separating sensed depolarizations of said atrium;
first timing means for defining first intervals initiated in response to sensed depolarizations of said atrium;
pulse generator means for generating pacing pulses in response to expiration of said first intervals;
second timing means for defining second intervals shorter than said first intervals, following sensed atrial depolarizations;
means responsive to a sensed depolarization of the atrium at one of said first and second locations, outside of a said second interval, for triggering said pulse generator to apply a cardiac pacing pulse to both of said first and second electrodes and for restarting a said first interval and responsive to a sensed atrial depolarization within a said second interval for restarting a said first interval without triggering said pulse generator means to apply a cardiac pacing pulse.

24. An apparatus [according to claim 22 wherein said responsive means comprises] for pacing the atrium, comprising:
first electrode means for location at a first location in the atrium;
second electrode means for location at a second location in the atrium;
means coupled to said first and second electrode means for sensing depolarizations of said atrium at said first and second locations;

means for measuring intervals separating sensed depolarizations of said atrium;

first timing means for defining first intervals initiated in response to sensed depolarizations of said atrium;

pulse generator means for generating pacing pulses in response to expiration of said first intervals;

second timing means for defining second intervals shorter than said first intervals, following sensed atrial depolarizations;

means responsive to a sensed depolarization of the atrium at one of said first and second locations, outside of a said second interval, for triggering said pulse generator to apply a cardiac pacing pulse to both of said first and second electrodes and for restarting a said first interval and responsive to a sensed atrial depolarization within a said second interval for restarting a said first interval without triggering said pulse generator means to apply a cardiac pacing pulse.

25. An apparatus according to claim 22 or claim 23 or claim 24 wherein said responsive means comprises means for applying a cardiac pacing pulse following a delay after a sensed depolarization of said atrium.

26. Apparatus according to claim 22 or claim 23 or claim 24, further comprising:

means for measuring intervals separating sensed depolarizations of said atrium; and means for defining said second time intervals following as a function of said measured intervals.

* * * * *